(12) United States Patent  
Viswanathan et al.

(10) Patent No.: US 8,992,546 B2  
(45) Date of Patent: Mar. 31, 2015

(54) ELECTROSTRICTION DEVICES AND METHODS FOR ASSISTED MAGNETIC NAVIGATION

(71) Applicants: Raju R. Viswanathan, Saint Louis, MO (US); Rogers C. Ritter, Saint Louis, MO (US)

(72) Inventors: Raju R. Viswanathan, Saint Louis, MO (US); Rogers C. Ritter, Saint Louis, MO (US); Peter R. Werp, Saint Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 14/043,387

(22) Filed: Oct. 1, 2013

(65) Prior Publication Data

US 2014/0107661 A1 Apr. 17, 2014

Related U.S. Application Data

(63) Continuation of application No. 11/770,547, filed on Jun. 28, 2007, now Pat. No. 8,551,109.

(60) Provisional application No. 60/817,063, filed on Jun. 28, 2006.

(51) Int. Cl.
*A61F 11/00* (2006.01)
*A61B 19/00* (2006.01)
*A61B 17/00* (2006.01)

(52) U.S. Cl.
CPC ....... *A61B 19/22* (2013.01); *A61B 2017/00106* (2013.01); *A61B 2017/003* (2013.01); *A61B 2019/2253* (2013.01)
USPC ......................................... 606/108

(58) Field of Classification Search
CPC ........... A61B 1/00158; A61B 1/00147; A61B 5/062; A61B 2017/00876; A61B 2019/2253; A61B 2017/00106; A61B 2017/003; A61B 19/22; A61F 2/025; A61F 2/02; A61F 2002/30668; A61F 2002/6863; A61F 2250/0001
USPC ......... 606/108, 191, 192, 194, 195, 198, 200; 623/1.1, 1.11, 1.12, 1.13, 1.14, 1.15, 623/1.16, 1.17, 1.18, 1.19, 1.2, 1.21, 1.22, 623/1.23
See application file for complete search history.

(56) References Cited

U.S. PATENT DOCUMENTS 4,869,247 A 9/1989 Howard, III et al.
5,125,888 A 6/1992 Howard et al.
(Continued)

OTHER PUBLICATIONS

International Search Report and Written Opinion for PCT/US07/72397 dated Jul. 11, 2008.

*Primary Examiner* — Jonathan W Miles
(74) *Attorney, Agent, or Firm* — Harness, Dickey & Pierce, P.L.C.

(57) ABSTRACT

An apparatus and method for interventional navigation within a subject's body is provided in which a medical device having at least one electrostrictive element is adapted to cause the distal end of the medical device to bend in a given direction for improving navigation. The medical device may further comprise at least one magnetically responsive element on the distal end, which may be oriented in the approximate direction of a magnetic field that is applied to the subject's body. At least one method for navigating a medical device though a subject's body is provided, by changing the direction of an applied magnetic field to align a magnetically responsive element on the distal end for orienting the distal end, and by applying a voltage to at least one electrostrictive element disposed in the distal portion of the device for causing the distal end to change orientation from that achieved by application of the magnetic field alone.

7 Claims, 11 Drawing Sheets

(56) References Cited

U.S. PATENT DOCUMENTS

| | | |
|---|---|---|
| 6,216,026 B1 | 4/2001 | Kuhn et al. |
| 6,304,769 B1 | 10/2001 | Arenson et al. |
| 6,401,723 B1 | 6/2002 | Garibaldi et al. |
| 6,679,836 B2 | 1/2004 | Couvillon, Jr. |
| 6,786,219 B2 | 9/2004 | Garibaldi et al. |
| 6,834,201 B2 | 12/2004 | Gillies et al. |
| 7,248,914 B2 | 7/2007 | Hastings et al. |
| 2004/0068173 A1 | 4/2004 | Viswanathan |
| 2004/0186376 A1 | 9/2004 | Hogg et al. |
| 2005/0113812 A1 | 5/2005 | Viswanathan et al. |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0074297 A1 | 4/2006 | Viswanathan |
| 2006/0094956 A1 | 5/2006 | Viswanathan |
| 2006/0100505 A1 | 5/2006 | Viswanathan |
| 2006/0256398 A1 | 11/2006 | Ishimaru et al. |
| 2006/0270915 A1 | 11/2006 | Ritter et al. |
| 2006/0276867 A1 | 12/2006 | Viswanathan |
| 2007/0021742 A1 | 1/2007 | Viswanathan |
| 2007/0043455 A1 | 2/2007 | Viswanathan et al. |
| 2007/0055124 A1 | 3/2007 | Viswanathan et al. |
| 2007/0137656 A1 | 6/2007 | Viswanathan |
| 2007/0225589 A1 | 9/2007 | Viswanathan |
| 2008/0006280 A1 | 1/2008 | Aliberto et al. |

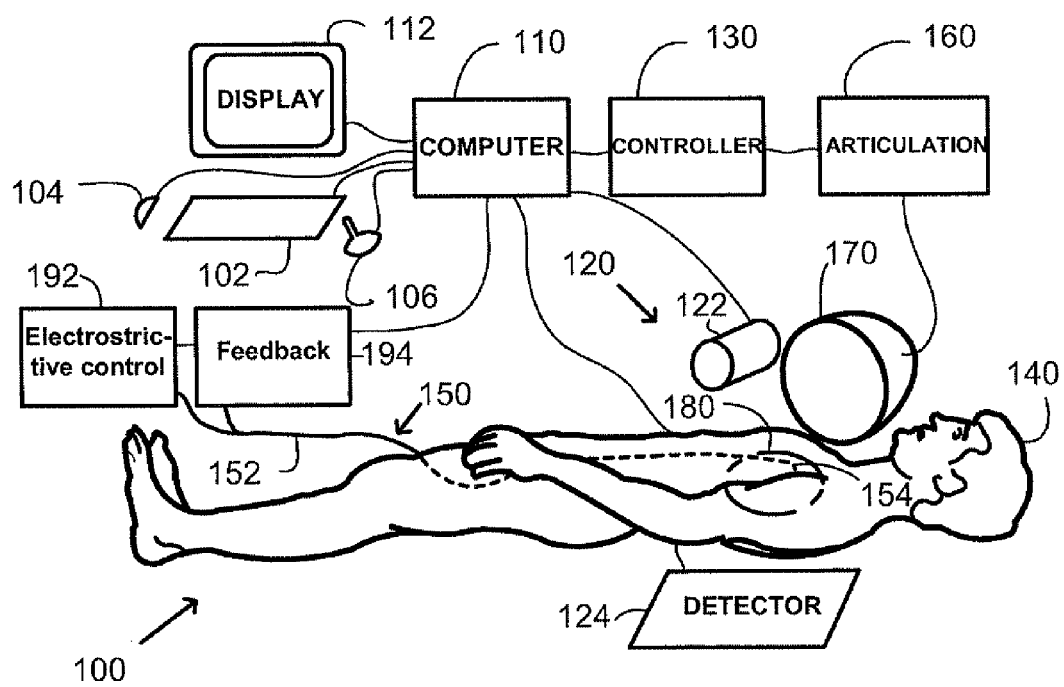
Fig. 1-A
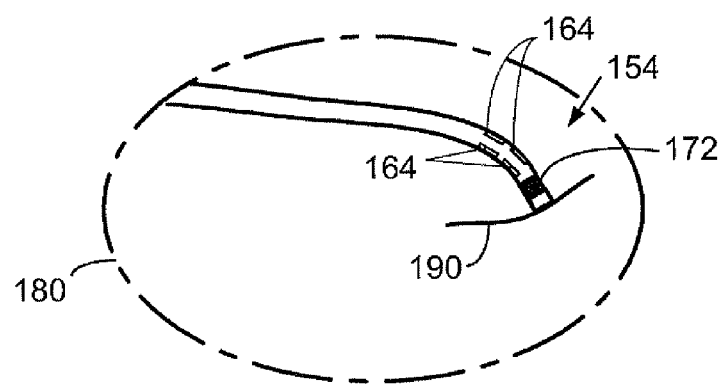
Fig. 1-B

ELECTROSTRICTION DEVICES AND METHODS FOR ASSISTED MAGNETIC NAVIGATION

CROSS-REFERENCE TO RELATED APPLICATIONS

This application claims the benefit of U.S. patent application Ser. No. 11/770,547, filed Jun. 28, 2007 which claims priority to U.S. Provisional Patent Application Ser. No. 60/817,063, filed Jun. 28, 2006. The disclosure of the above-referenced application is incorporated herein by reference.

FIELD OF THE INVENTION

The present disclosure relates to navigation of medical devices within a subject's body, and more particularly to the use of electrostrictive components in magnetically navigable medical devices.

BACKGROUND OF THE INVENTION

A variety of techniques are currently available to physicians for controlling elongate medical devices such as catheters, endoscopes and other surgical tools within a patient. For example, magnetic steering techniques provide computer-assisted control of a catheter tip while allowing an operating physician to remain outside the operating room x-ray field. In such systems, there is often a lag between the direction of an applied magnetic field and the actual orientation of the distal end of the medical device that must be taken into account for navigation. Typically, the physician will advance the device only once the distal end of the medical device is in the desired orientation, which magnetic steering techniques may not always achieve by themselves: the applied torque might not be sufficient to overcome resistance, as for instance in areas of rapid blood flow; proximal device advancement might be ineffective due to device prolapse or buckling at a vessel branch. Further, magnetic navigation might not prevent dislodgment, for instance when a guide catheter has been inserted to a coronary ostium, and an interventional device is advanced past the guide catheter distal end; resistance to advancement might cause the guide catheter to become dislodged, and at the present time it is not possible to precisely control the magnetic field applied at the ostium when magnetically navigating the interventional device distal tip beyond the guide catheter distal tip. In endocardial applications using current magnetic navigation technologies, it might be difficult to maintain contact between an interventional device distal end and the moving heart wall, in particular upon oblique or glancing approaches where the distal end is not perpendicular to the tissue. U.S. Pat. No. 6,679,836 issued to Couvillon and assigned to SciMed Life Systems, Inc., describes a guide catheter apparatus comprising a plurality of electro-active polymer actuators disposed along its length, and methods of using the same; however that patent does not teach nor suggest the combinative use of electrostrictive materials with magnetic navigation. Similarly, published U.S. patent application No. 20050256398, filed by Hastings et al., describes methods and systems for interventional medicine, including the use of electrostriction to bend a medical device or selectively stiffen a medical device. Although that patent application does describe methods of magnetically navigating an interventional medical device, it does not teach nor suggest the combinative use of electrostriction with magnetic navigation. Combinative use of these approaches, as disclosed below, significantly improves upon the state-of-the-art and enables applications that could not have been successfully performed before.

Another motivation for the present invention is the possibility of improving the performance of a magnetic navigation system while reducing its size and cost. For example, reducing the size of the magnetic source magnets, made possible by electrostrictive torques applied at particular angles, could provide greater imaging and physician access. For example, the tip force required in certain ablation procedures in the heart, may be limited by the size of the source magnets, and can be improved by the addition of electrostriction.

SUMMARY OF THE INVENTION

The present invention relates to medical devices having one or more actuators for bending or stiffening specific portions of the medical device for enhancing methods of magnetic navigation within a subject's body. In the various embodiments, devices and methods for magnetic navigation of a medical device within a subject's body are provided that employ electrostrictive behavior. In a first embodiment of a medical device, the device includes at least one electrostrictive element disposed on or near its distal end that is adapted to cause the distal end to bend in a given direction. The medical device further comprises at least one magnetically responsive element on the distal end, which may be oriented in the direction of an externally applied magnetic field.

In another aspect of the present invention, various embodiments of a method for magnetically navigating medical devices including at least one electrostrictive element are provided. In one embodiment of a method, the medical device may be magnetically navigated though a subject's body by changing the direction of an applied magnetic field, and by applying a voltage to at least one electrostrictive element disposed on or near the distal end to cause the distal end to change orientation from that achieved by application of the magnetic field alone. In another embodiment, a method is provided in which the medical device may be selectively stiffened by applying a voltage to at least one electrostrictive element on the device while simultaneously magnetically orienting the device distal end. In yet another embodiment, a method of magnetically navigating a medical device having a plurality of electrostrictive elements and a plurality of force or pressure sensors is provided. The pressure sensors enable sensing contact along a portion of the medical device with a tissue surface within the subject's body, such that select electrostrictive elements disposed along the medical device may be actuated in response to sensor activity for locally stiffening or bending the medical device. The method provides controlling an electrostriction-actuated elongate medical device by actuating one or more of the electrostrictive elements in response to a signal from a contact sensor. Accordingly, methods of magnetic navigation are described that minimize medical device deflection caused by contact with a tissue surface, or enhance the deflection of the medical device for reaching or contacting a target area within the subject's body, or improve other aspects of navigation within a subject's body.

A still further aspect of this invention is the inclusion of methods of determining positions and angles at which a device magnetic tip requires magnetic torques which are most difficult to provide by a magnetic system alone. It is known that certain locations of a device tip, and for certain initial angles, combined with the need for certain final turn directions, in addition to the need for larger tip force, become the limiting conditions that require stronger and larger source magnets.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

FIG. 1-A is a system block-diagram of a magnetic navigation interventional system for use of an electrostriction-assisted interventional medical device according to the principles of the present invention;

FIG. 1-B shows electrostrictive elements arranged on segments of an interventional device designed according to the principles of the present invention;

Throughout the drawings, corresponding reference numerals indicate like or corresponding parts and features.

DETAILED DESCRIPTION OF THE INVENTION

Figure 2:
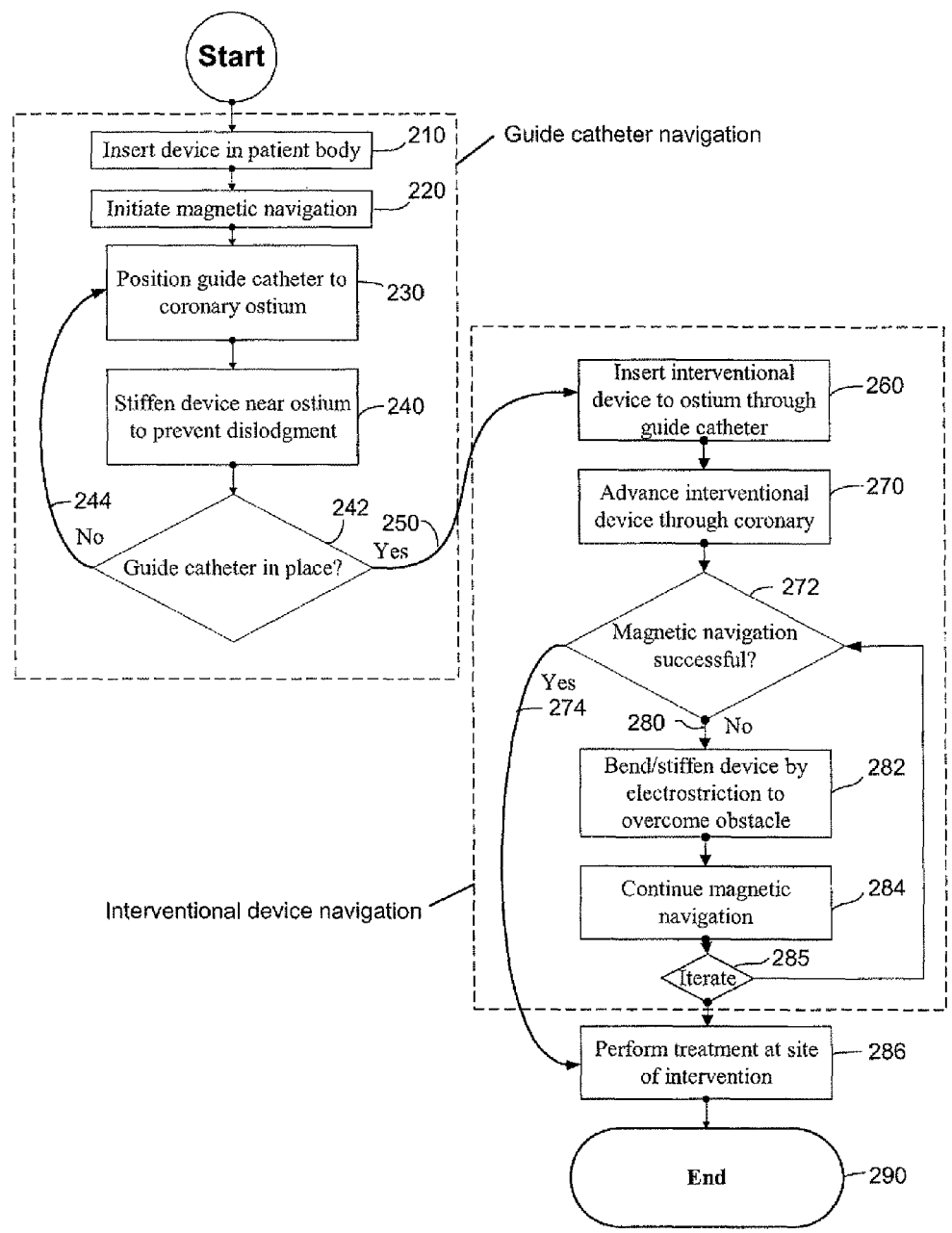
FIG. 2 is a flow-chart of the navigation process for a guide catheter navigation and placement and subsequent navigation of an interventional device through and beyond the guide catheter.

The various embodiments provide for devices and methods of enhanced magnetic navigation of a medical device within a subject's body through the use of electrostrictive behavior. Electrostrictive behavior provides an additional means of controlling a segment of a medical device (e.g. catheter, endoscope, guide wire, guide catheter, sheath, or electrode) for navigation in the body. Electrostrictive materials are those in which application of a voltage will result in a dimension change (expansion or contraction, depending on the material). The effect of applying a voltage difference to an electrostrictive material is not inverted by inverting the voltage polarity, as opposed to piezoelectric materials. The arrangement of electrostrictive material on the medical device provides for their use in deflecting the medical device distal end for navigational purposes. Electrostrictive control requires application of a controlling variable from an external electrical power source(s) to the segment electrostrictive components, to create the desired strains and consequent bending or stiffening of the medical device. The control variables may be a voltage or current applied to one or more electrostrictive elements or piezoelectric elements disposed in the medical device. The distal tip of a medical device may include electrostrictive polymers, for example, which when contracted cause deflection of the distal tip. The electrostrictive component is connected to electrical leads that extend from the proximal end to the distal end of the medical device.

An elongated navigable medical device 150 having a proximal end 152 and a distal end 154 is provided for use in an interventional system 100, FIG. 1-A. A patient 140 is positioned within the interventional system, and the medical device is inserted into a blood vessel of the patient and navigated to an intervention volume 180. In magnetic navigation a magnetic field externally generated by magnet(s) 170 orients a small magnet located at the device distal end (172, FIG. 1-B). Real time information is provided to the physician, for example by an x-ray imaging chain 120 comprising an x-ray tube 122 and an x-ray detector 124, and also possibly by use of a three-dimensional device localization system such as a set of electromagnetic transmitters/emitters located at the device distal end (not shown) and associated external electromagnetic receivers, or other localization device with similar effect. The physician provides inputs to the navigation system through a navigation computer 110 comprising user interface devices such as a display system 112, a keyboard 102, mouse 104, joystick 106, and similar input devices. Display 112 also shows real-time image information acquired by the imaging chain 120 and the three-dimensional localization system. Computer 110 relays inputs from the user or from a control computer imbedded in navigation computer 110 to a controller 130 that determines and actuates the magnet(s) orientation through articulation control 160. As shown in FIG. 1-B, electrostrictive element(s) 164 located along the device length are activated to help in navigation, for example by bending or stiffening the device. Electrostriction controller 192 communicates with navigation computer 110, and also with the physician through the user interface previously described, and controls the application of control voltages to the electrostrictive element(s). In specific embodiments, device tip 154 also has sensor(s) (not shown), such as strain gauges or similar devices located at or near the device tip to provide force data information to estimate the amount of pressure applied on the target tissue 190, as feedback to system 100 in assisting navigation; other sensors might include an ultrasound device or other device appropriate for the determination of distance from the device tip to the tissue. Yet other force sensors may be provided along various device segments to measure the amount of force exerted by the subject's tissues onto the device. Such sensors signals including feedback data from the tip element and the device distal end are processed by feedback block 194 which in turn communicates with the electrostrictive control block 192 as well as with computer 110 comprising a control computer. Further device tip feedback data include relative tip and tissue positional information provided by an imaging system, predictive device modeling, or device localization system. In closed loop implementation, the electrostrictive control 192 automatically provides input commands to the device electrostrictive elements based on feedback data and previously provided input instructions; in semi-closed loop implementations, the physician fine-tunes the navigation control, based in part upon feedback data. Control commands and feedback data may be communicated from the user interface and control 192 to the device and from the device back to the feedback block 194, through cables or other means, such as wireless communications and interfaces. As known in the art, system 100 comprises an electromechanical device advancer (not shown), capable of precise device advance and retraction based on corresponding control commands.

In another aspect of the invention, a method is disclosed that enables electrostriction-assisted magnetic navigation of an interventional device to a theater of operation and subsequent acquisition of diagnostic information and/or treatment of specific conditions. FIG. 2 provides a flowchart for an exemplary embodiment of the method. In this application, the objective of the intervention is the treatment of a coronary occlusion, such as a chronic total occlusion. The intervention proceeds in three steps, first insertion of a guide catheter through the vasculature to the coronary ostium, followed by insertion of an interventional device through the guide catheter to the occlusion, and third treatment at the site of occlusion. The two navigation steps are depicted in FIG. 2. First, the guide catheter is inserted in the subject's body, 210. Magnetic navigation is initiated, guiding the distal guide catheter tip in a series of steps with concurrent or subsequent proximal device advance, 220. Next, the guide catheter tip is positioned at the coronary ostium, 230. To prevent dislodgement, as often occurs when inserting an interventional device through the guide catheter, selective guide catheter stiffening is affected through electrostrictive actuation of specific elements on the guide catheter, 240. In step 242, it is confirmed that the guide catheter is firmly in place at the ostium. If not, 244, the method iterates through steps 230 and 240 to attain this objective, and then proceeds, 250, to the second navigation sequence. In the next step, the interventional device is inserted through the guide catheter to the ostium, 260. Then the interventional device is advanced and navigated, 270, beyond the guide catheter distal end and through the coronary artery toward the occlusion. If the magnetic navigation is successful, 274, the method proceeds to the third step, 286, performance of the treatment at the intervention site. Otherwise, 280, the interventional device is bent or stiffened by electrostriction of selected elements as necessary to facilitate navigation to the occlusion, 282. Once a difficult turn or advance has been made, magnetic navigation resumes 284, and these steps are iterated 285 till the interventional device is successfully positioned at the site of treatment, treatment takes place 286, and the method terminates 290.

Figure 3:
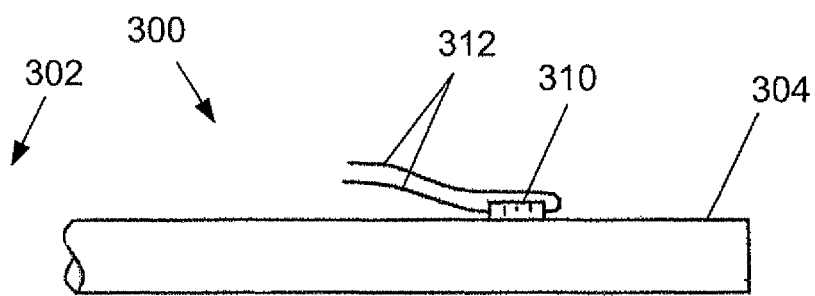
FIG. 3 is a side elevation view of a portion of one embodiment of a medical device comprising one electrostrictive element according to the principles disclosed in the present application.

In a first embodiment of a medical device 300 shown in FIG. 3, at least one electrostrictive element 310 is disposed on a portion or side of the distal end 304 of the medical device 300. The electrostrictive element 310 is adapted to cause the distal end 304 to bend in a given direction. Electrical energy transmitted through fine wires 312 extending along the length of the medical device 300 from the proximal end 302 activates piezoelectric or electrostrictive actuator elements. Although wires and electrostrictive elements are shown for illustration as being external to the device 300 structure, it is understood that preferably element 310 is embedded within the device wall or within the device so that it does not protrude externally; and similarly wires 312 run within the device wall or lumen. A similar remark applies to FIGS. 4 to 7. The application of an electric potential across the electrostrictive element 310 causes the electrostrictive element 310 to change dimension, in turn causing the medical device 300 to bend. The bending action at the wall could occur either because the device 300 itself would bend upon application of voltage, or by affixing an element 310 to another element which could bend but not stretch or compress. The medical device 300 could then be twisted at the proximal end 302 to effect a turn in any direction. The deflection or manipulation of such a medical device 300 would be somewhat limited however, in particular as torque applied at the device proximal end does not always propagate effectively to the distal end. The medical device 300 may be used in combination with a delivery sheath (not shown) that comprises at least one magnetically responsive element on or near its distal end. The magnetically responsive element disposed on the distal end of the delivery sheath may be oriented in a desired direction by application of a magnetic field, which aligns the magnetically responsive element with the field direction. Accordingly, the delivery sheath may be magnetically navigated though a subject's body by changing the direction of an applied magnetic field that is applied to the subject's body in which the delivery sheath is introduced. Conversely, electrostrictive elements may be placed along the length of a delivery sheath, while a catheter or other medical device designed to be inserted through the delivery sheath may be magnetically guided, at least when advancing beyond the distal end of the delivery sheath. Generally speaking, magnetic and electrostrictive elements may be placed by themselves or in combination along any portion of a medical device; the medical device being one of a guide catheter, catheter, sheath, guide wire, interventional device, endoscope, surgery device, or any interventional medical device designed to be inserted in a subject's body cavity.

Where a delivery sheath, guide catheter, or similar interventional device encounters difficulty during magnetic navigation, the medical device 300 may be employed in combination with the delivery sheath for navigating towards a target area within the subject's body. One embodiment of a method is provided for navigating such a medical device 300 in the body. The method comprises magnetically navigating a delivery sheath to a selected orientation by applying a magnetic field to orient a magnetically responsive element in the distal end portion of the sheath, and advancing the sheath. The method further provides for advancing the distal end of a flexible medical device 300 within the delivery sheath from the distal end of the delivery sheath. By applying a voltage to at least one electrostrictive element 310 on the flexible medical device 300, the distal end 304 of the medical device 300 may be changed in shape, to guide the medical device 300 (and also possibly the delivery sheath) in a selected direction. Conversely, a delivery sheath, guide catheter, or similar interventional device might be navigated by actuating electrostrictive elements placed thereon, while a catheter or other medical device designed to be inserted through the delivery sheath maybe magnetically guided, at least when advancing beyond the distal end of the delivery sheath.

Figure 4:
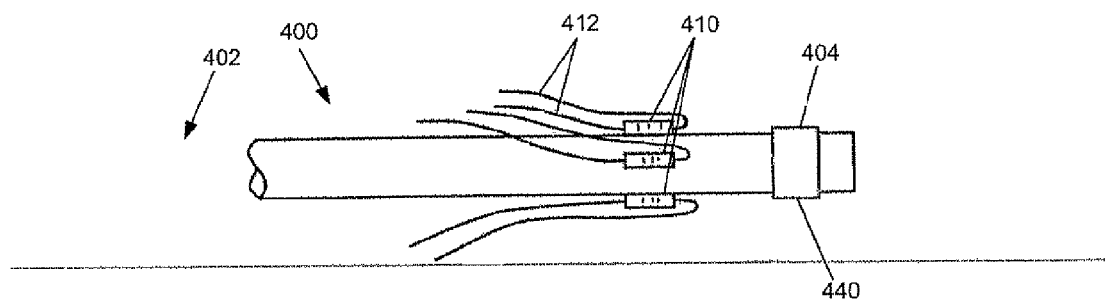
FIG. 4 is a side elevation view of a portion of a second embodiment of a medical device comprising a plurality of electrostrictive elements disposed around part of the device circumference.
Figure 5:
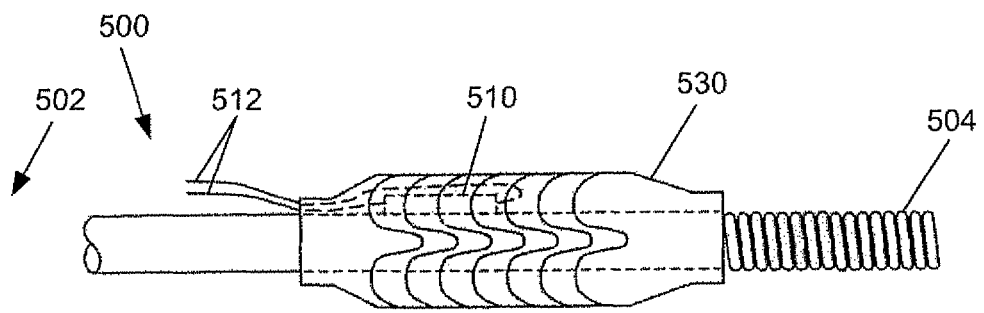
FIG. 5 is a side elevation view of a portion of a third embodiment of a medical device comprising a plurality of electrostrictive elements for deployment of a stent.

A preferred embodiment of a medical device might comprise a plurality of electrostrictive elements 410 affixed about a circumference of the exterior of the medical device 400 as in FIG. 4. Combinations of voltages applied to the electrostrictive elements 410 could then deflect the distal end 404 of the medical device 400 in any direction without requiring twisting the proximal end 402. In a second embodiment of a medical device 400, the medical device 400 comprises at least two electrostrictive elements 410 disposed on a portion or side of the distal end 404 of the medical device 400, causing the distal end 404 to bend in a given direction. Symmetric placements of a multiplicity of such elements around the device circumference can provide bending capability in a range of bending planes or across several bending planes.

The medical device 400 may further comprise at least one magnetically responsive element 440 on or near the distal end portion 404. The magnetically responsive element 440 disposed on the distal end portion 404 of the medical device 400 may be oriented in the direction of an externally applied magnetic field. Accordingly, the medical device 400 may be magnetically navigated though a subject's body by changing the direction of an applied magnetic field to guide the medical device 400. Likewise, a magnetically navigable delivery sheath may be used in combination with the medical device. The delivery sheath preferably comprises at least one electrostrictive element disposed on a portion or side of the distal end of the sheath, for causing the distal end to bend in a given direction.

Accordingly, at least one embodiment of a method for navigating such a medical device 400 and a delivery sheath, guide catheter, or similar interventional device within a subject's body is provided. The method provides for electrostrictively navigating a delivery sheath to a selected orientation by applying a voltage to one or more electrostrictive elements on the sheath to orient the distal end portion of the sheath and advancing the sheath, and advancing the distal end of a flexible medical device 400 from the distal end of the sheath, and applying a magnetic field to orient a magnetically responsive element 440 in the distal end portion 404 of the device 400 to orient the distal end of the medical device 400 in a selected direction. The method may further comprise applying a voltage to at least one electrostrictive element 410 to cause the distal end 404 to bend in a select direction.

With the second embodiment of a medical device 400, a method for navigating the medical device 400 within a subject's body without the use of a delivery sheath is also provided. The method comprises successively orienting the distal end 404 of the medical device 400 by applying a magnetic field to orient a magnetically responsive element 440 in the distal end portion 404 of the device 400. The method further comprises applying a voltage to at least one electrostrictive element 410 on the medical device 400 to change the orientation of the distal end 404 from the orientation achieved by the application of the magnetic field alone. Thus, the medical device 400 may be advanced upon achieving the desired orientation of the distal end 404 using the above methods. A method is also provided for navigating the medical device 400 in which the medical device 400 may be selectively stiffened to assist in advancing or pushing the medical device 400 through the subject's body. In this embodiment of a method for navigation, the method of navigating comprises orienting the distal end 404 of the medical device 400 by applying a magnetic field to orient a magnetically responsive element 420 in the distal end portion 404 of the device 400. The method further comprises advancing the device 400, and applying a voltage to at least one electrostrictive element 410 on the device 400 to selectively stiffen a portion of the medical device 400.

Similarly, an improved method of magnetically navigating a medical device 400 having at least one magnetically responsive element 440 and at least one electrostrictive element 410 disposed on or near the distal end portion 404 of the device 400 is provided. The method comprises successively orienting the distal end 404 of the medical device 400 by applying a magnetic field to orient a magnetically responsive element 440 in the distal end portion of the device 400. The method further comprises applying a voltage to the at least one electrostrictive element 410 of the medical device 400 to selectively shape a portion of the medical device 400 to change the orientation achieved by the application of the magnetic field alone. Accordingly, the medical device 400 may be advanced upon orienting the distal end 404 of the medical device 400 by utilizing the magnetically responsive element 440, the electrostrictive element 410, or both.

A stent catheter for delivering a stent 530 in the body may also be used in accordance with the principles of the present invention. In a third embodiment of a medical device, the device is a stent catheter 500 including a landing for supporting a stent 530 thereon, and at least one electrostrictive element 510 in the landing to facilitate bending of the catheter 500 in the vicinity of the landing upon application of a voltage to the electrostrictive element 510.

Accordingly, a method of placing a stent 530 in the vasculature of a subject is provided. The method of placing a stent 530 in the vasculature in a subject comprises navigating the distal end 504 of a catheter 500 carrying the stent 530 through the vasculature by operating one or more actuators 510 to orient the distal end portion 504 of the catheter 500, and advancing the catheter. The catheter 500 may comprise one or more electrostrictive actuator elements 510 under the stent 530 which may be actuated together to facilitate bending of the catheter 500 and stent 530. The one or more actuators 510 may be operated by applying voltage to at least one electrostrictive actuator element 510 on the catheter 500. In another embodiment of a method of placing a stent 530 in the vasculature in a subject, the method comprises navigating the distal end 504 of a stent delivery catheter 500 carrying the stent through the vasculature by applying a magnetic field to orient a magnetically responsive element (not shown) on the distal end portion of the catheter 500. The method may further comprise applying a voltage to at least one electrostrictive element 510 to facilitate the bending of the catheter 500 and stent 530. Thus, the medical device 500 may be advanced upon orienting the distal end 504 of the medical device 500 by employing the magnetically responsive element, the electrostrictive element 510, or both.

Figure 6:
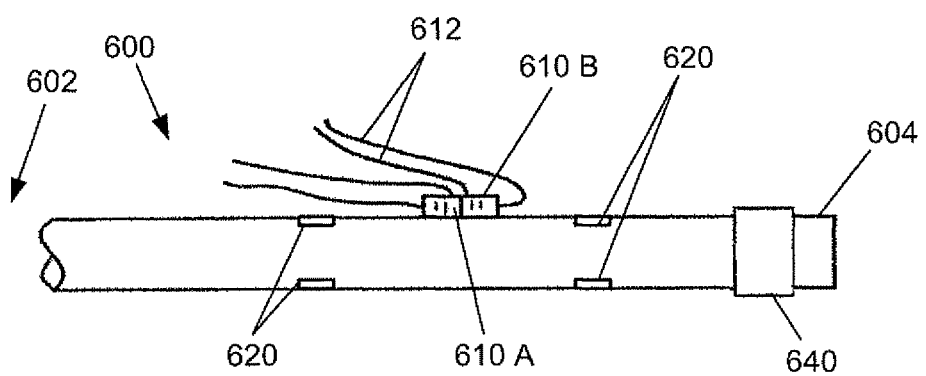
FIG. 6 is a side elevation view of a portion of a fourth embodiment of a medical device with two electrostrictive elements mechanically in series but electrically in parallel.

In a fourth embodiment of a magnetically navigable medical device shown in FIG. 6, the medical device 600 comprises a plurality of electrostrictive elements 610 disposed on or near the distal end portion 604, and a plurality of contact sensors 620 disposed on or near the distal end portion 604, or near electrostrictive element(s) 610. The medical device 600 includes at least one magnetically responsive element 640 associated with the distal end 604 of the device 600, which may orient the device 600 upon application of a magnetic field in a selected direction. The magnetically responsive element 640 is of a sufficient size, shape, and magnetic characteristics to cause the distal end 604 of the medical device 600 to be oriented in a selected direction in response to an applied magnetic field of preferably no more than about 0.1 Tesla, and more preferably no more than about 0.08 Tesla, and more preferably no more than about 0.06 Tesla.

When actuated, the electrostrictive elements 610 change the flexibility or shape of the medical device. In the particular embodiment illustrated, the electrostrictive elements 610 may act mechanically in series, but are electrically in parallel for actuating each electrostrictive element as shown in FIG. 6. This configuration increases the total bend angle that could be attained for a given voltage application.

Accordingly, a method of navigating an elongated medical device is provided, whereby navigation is effected through a combination of magnetic navigation and selective electrostrictive bending or stiffening of at least a device segment. Electrostrictive actuation is determined by the user, a control computer based on input instructions, or a user or control computer based on feedback from contact sensor(s). Application of electrostrictive bending or stiffening serves to control the amount of contact force between part of the device and the vessel or body cavity wall.

Figure 7:
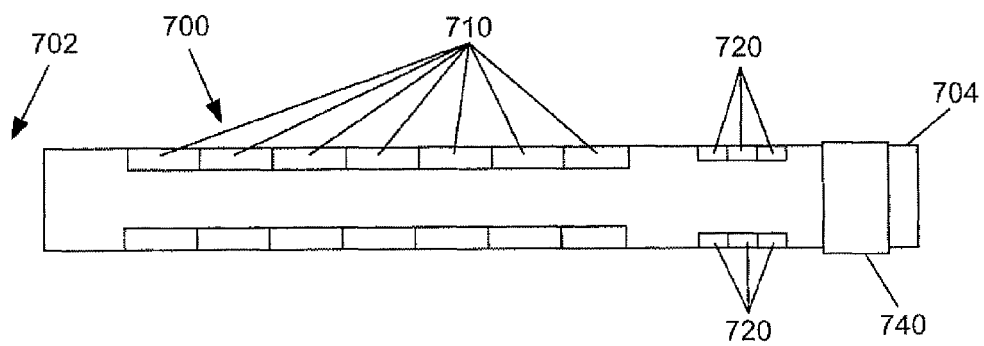
FIG. 7 is a side elevation view of a portion of a fifth embodiment of a medical device comprising a plurality of electrostrictive elements arranged along part of the length of the medical device according to the principles disclosed in the present application.

In a fifth embodiment of a medical device shown in FIG. 7, the medical device 700 comprises a plurality of electrostrictive elements 710 along at least a segment of the medical device. Several of the electrostrictive actuating elements 710 may be electrically connected in parallel to each other, and several of the electrostrictive actuating elements 710 may be connected in series. The plurality of electrostrictive elements 710 may comprise a plurality of embedded electrostrictive actuating members that are embedded within the outer portion or within the wall of the elongate medical device 700. A useful arrangement of elements might act not at a single location along a catheter, but instead may comprise one or more strip(s) of elements along a side of a device as shown in FIG. 7. Each element 710 of the strip is mechanically in series with a next element 710 of the same strip, but may be electrically connected in parallel or in series. Using one or more strips, as in FIG. 7, would provide for more effective bending or turning of the medical device 700. The construction of such strips might take advantage of methods used in the semiconductor industry. In this embodiment various electrostrictive elements might have various transfer functions (ratio of bend to applied voltage) along each strip so as to provide for a non-uniform bending of a medical device 700 having a uniform bending stiffness. The same effect could be achieved with a medical device 700 of variable stiffness and strips of uniformly responsive electrostrictive elements 710; that configuration might be undesirable for medical reasons in specific applications. The plurality of strips having electrostrictive actuating elements 710 may be connected in at least two groups, each of which when actuated causes the medical device 700 to assume a predetermined configuration.

Accordingly, an improved method for navigating a medical device 700 having at least one magnetically responsive element 740 and a plurality of electrostrictive elements 710 is also provided. The improved method comprises using an externally applied magnetic field of no more than about 0.1 Tesla, and more preferably no more than about 0.08 Tesla, and more preferably no more than about 0.06 Tesla, to orient the magnetically responsive element 740 and the distal end 704 of the medical device 700. The method further comprises applying a voltage to at least one electrostrictive element 710 on the device 700 to change the orientation of the distal end 704 of the medical device 700 if the magnetic field is insufficient to orient the device 700 in the desired direction. Thus, the method also provides for improved navigation of a magnetically navigable medical device 700 with application of magnetic fields of reduced magnitude to the subject's body. The method also provides for improved navigation in magnetic fields of various magnitudes, by allowing design of reduced size magnetic tips that more easily navigate convoluted anatomy or narrow lumen. Similarly, an improved method of navigating a medical device 700 in an externally applied magnetic field is provided, by applying a voltage to at least one electrostrictive element 710 to change the orientation of the medical device 700 in a direction of which the magnetic field is not able to attain. An example of such a direction is one having a component parallel to a "forbidden plane" of a magnetic navigation system. When attempting to perform magnetic navigation using a Magnetic Resonance Imaging (MRI) system, the main static field is typically oriented along the patient's longitudinal axis. A device tip located for example in a plane orthogonal to the static field axis (the forbidden plane), cannot be re-oriented in that plane by using the static magnetic field alone; indeed the torque applied by the static field is always orthogonal to the field axis, and therefore cannot induce rotation around the static field axis. Use of electrostrictive orientation allows navigation in such a system, including navigation in the forbidden plane.

In each of the above embodiments of a medical device, little energy is required in electrostrictive activity (current only flows while the molecular constituents achieve their strained condition or while changing the strained condition). Fine wires can be used, and one skilled in electromagnetism would know how to insulate them so that voltages would not cause arcing or otherwise endanger a patient. Furthermore, the wires may be embedded within the side of the medical device, or may extend through a lumen within the medical device to the proximal end of the device. Likewise, by appropriate design as known in the art, application of electrical energy to the electrostrictive elements does not affect any sensors that may be employed within the subject's body.

In the fifth embodiment discussed above, the magnetically navigable elongate medical device 700 may further include a plurality of contact sensors 720 for sensing contact of the medical device 700 with a tissue wall. The contact sensors 720 may be stress sensors that detect a force acting on the medical device, and provide an output indicative of the level of force. The contact sensors 720 may also be strain gauges that detect deflection of the distal portion 704 of the medical device 700 upon contacting a surface within a subject's body. In the magnetically navigable elongate medical device 700, the signals associated with the sensing and actuating elements are connected by fine wires (not shown) embedded in a non-conducting material on the medical device. The sensors 720 of the medical device 700 enable sensing of contact along a portion of the medical device 700 with a tissue surface within the subject's body, such that an electrostrictive element 710 disposed along that portion of the medical device 700 may be actuated to stiffen or alternatively bend the portion that has been contacted. The sensors 720 accordingly allow for controlling or minimizing the amount of deflection of the medical device 700 caused by contact along a portion of the device with a tissue surface within the subject's body.

Accordingly, an improved method of navigating such a medical device 700 having a plurality of electrostrictive elements 710 and a plurality of sensors 720 is provided. The method provides controlling an electrostrictively actuated elongate medical device 700 by actuating one or more of the electrostrictive elements 710 in response to a signal from a contact sensor 720, to selectively stiffen or alternatively bend the medical device 700 in the vicinity of the sensed contact. Other embodiments of the method may further control the contact between the distal end 704 of an elongate medical device 700 and a moving anatomical surface, such as a beating heart wall or an expanding lung wall. The method comprises applying a time-varying voltage to at least one electrostrictive element 710 on the medical device 700 to change the configuration of the medical device 700 as the anatomical surface moves, to maintain contact between the medical device 700 and the surface. Where the anatomical surface is the surface of the heart, the application of voltage may be gated with an electrocardiogram signal such that the electrostrictive element 710 is actuated as the heart beats to bend the distal end portion 704 to maintain contact of the medical device 700 against the heart surface.

In yet another embodiment of a method in accordance with the principles of the present invention, a method for circumscribing a path of contact on a tissue surface is provided. In one or more of the afore mentioned embodiments of a medical device 700 having at least one electrostrictive element 710, a method is provided for establishing contact with an anatomical surface in a ring pattern. The method comprises magnetically orienting an elongate medical device 700 toward the center of an intended circle of contact on a tissue surface, and applying a voltage to at least one electrostrictive element 710 near the device 700 distal end. The activation of the electrostrictive element 710 causes the medical device 700 to deflect or bend into a position of contact with the tissue surface. The medical device 700 may either be rotated by proximal torque application to circumscribe a circle about the longitudinal axis of the medical device 700, or a plurality of electrostrictive elements 710 disposed around the axis of the medical device 700 may be alternately actuated to cause the device distal end to circumscribe a circle or arc of a circle about the initial distal longitudinal axis of the medical device. Alternatively, a method for contacting an anatomical surface in a ring pattern or arcs of a ring pattern is provided that includes orienting an elongate medical device 700 relative to the center of the ring by applying a voltage to at least one electrostrictive element 710 on the elongate medical device, and swinging or rotating the medical device about an arc by applying a changing magnetic field to the depending device tip to magnetically orient a magnetically responsive element 740 carried thereon, or applying torque at the device proximal end, or combinations thereof.

A medical device and navigation system combination is also provided for controlling the navigation of the medical device within a subject's body. The combination generally comprises an elongate medical device designed for magnetic navigation having a plurality of electrostrictive elements for selectively stiffening or bending portions of the device, and a plurality of contact sensors for sensing contact with the medical device. The combination further comprises a control for actuating one or more of the electrostrictive elements in response to a signal from a contact sensor, to selectively stiffen or bend a portion of the medical device in the vicinity of the sensed contact. The combination further comprises the use of magnets located at least at the device tip. The combination may employ any of the afore-mentioned embodiments of a medical device. The electrical connections to the electrostrictive elements and sensors of the medical device are in communication with the control via one or more connections, for enabling the feedback and control blocks to sense contact signals and to apply electrical signals to the electrostrictive elements. Alternatively, sensors data are provided through wireless connection, and power is supplied to the device by a power supply attached to the device proximal end. The combination of a medical device and navigation system accordingly facilitates stiffening a portion of the medical device to minimize the deflection of the medical device caused by contact with a tissue surface, enhances the ability to deflect the medical device to reach or contact a target area within the body, decreases device prolapse and dislodgement, and increases maneuverability.

Figure 8:
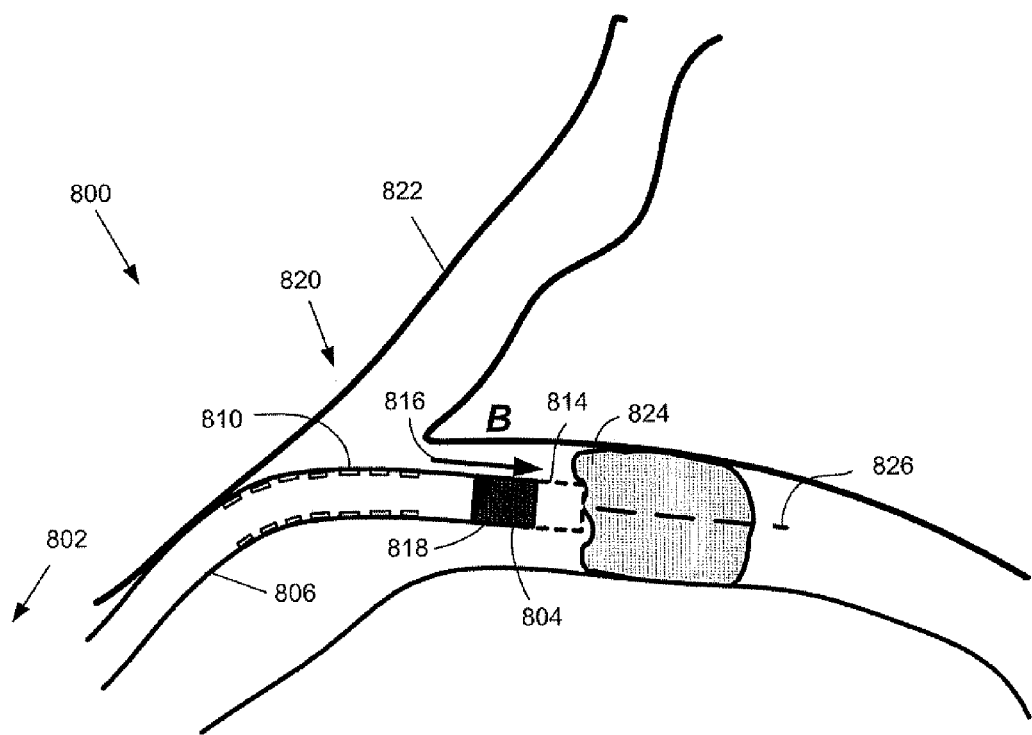
FIG. 8 shows application of the principles of the present invention to device prolapse prevention.

FIG. 8 illustrates application of the devices and methods of the present invention to interventional medical device prolapse prevention. In certain situations schematically represented by numeral 800, an interventional device 806 may have been magnetically navigated using externally generated magnetic field B 816 past a vessel confluence 820. The device distal tip 804 then encounters resistance to advancement; in FIG. 8 this resistance is due to an occlusion that needs to be traversed for therapy to be effective. Device design typically requires a trade-off between flexibility for maneuverability and stiffness to enable effective device advancement as well as proximally applied torque propagation. However, as mechanical force is proximally applied to advance the distal tip through the lesion, a device segment might prolapse into vessel branch 822. Under such condition, advancement force is no longer effectively transmitted to the distal tip but instead leads to further device prolapse. To prevent this, one or a plurality of electrostrictive elements 810 placed along the device length are actuated to stiffen the device segment located at or near the vessel bifurcation. Stiffening at the confluence reduces device flexibility, prevents prolapse, and enables force application at the lesion 824 along local vessel axis 826.

Figure 9:
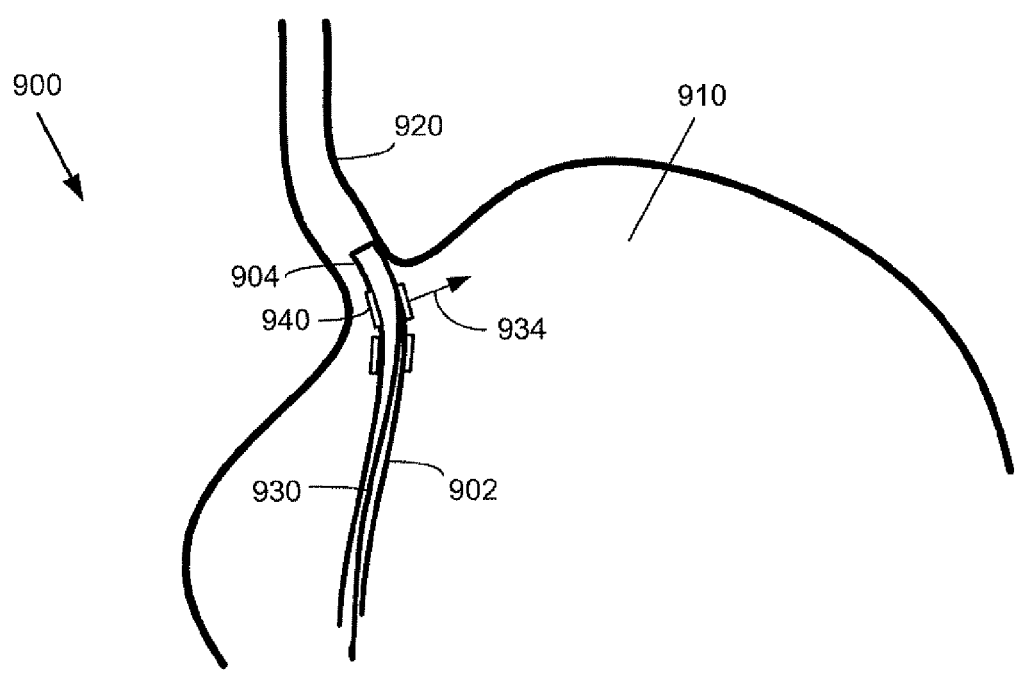
FIG. 9 shows application of the principles of the present invention to device dislodgment prevention.

Similarly, FIG. 9 illustrates schematically how selective device stiffening could prevent dislodgment. A medical device such as a guide catheter 902 is navigated through a chamber or body cavity 910 such that the guide catheter distal tip 204 is engaged at least partially in vessel or body lumen 920. The guide catheter distal end in the proximity of the lumen is curved such that upon advancement of an interventional device such as a catheter 930 a mechanical force is acted upon the guide catheter with a force component 934 orthogonal to the local guide catheter axis. This force component might dislodge the guide catheter distal tip 904 from the lumen, creating intervention complications and delays. Actuation of electrostrictive components 940 located at or near the guide catheter bend to stiffen the device, by themselves or in combination with other actions such as distal guide catheter force application, will prevent device dislodgment and thus improve intervention effectiveness and efficacy. Alternatively, dislodgment may occur due to motion of the beating heart; there again selective device stiffening by itself or in conjunction with distal guide catheter force application will be effective in preventing wall motion and/or flow to dislodge the device. Dislodgement may also occur when an interventional device is inserted through the guide catheter and progresses beyond the guide catheter distal end, and resistance to advancement is encountered; selective stiffening and/or bending of the guide catheter is effective in preventing resistance to result in guide catheter dislodgment.

Figure 10:
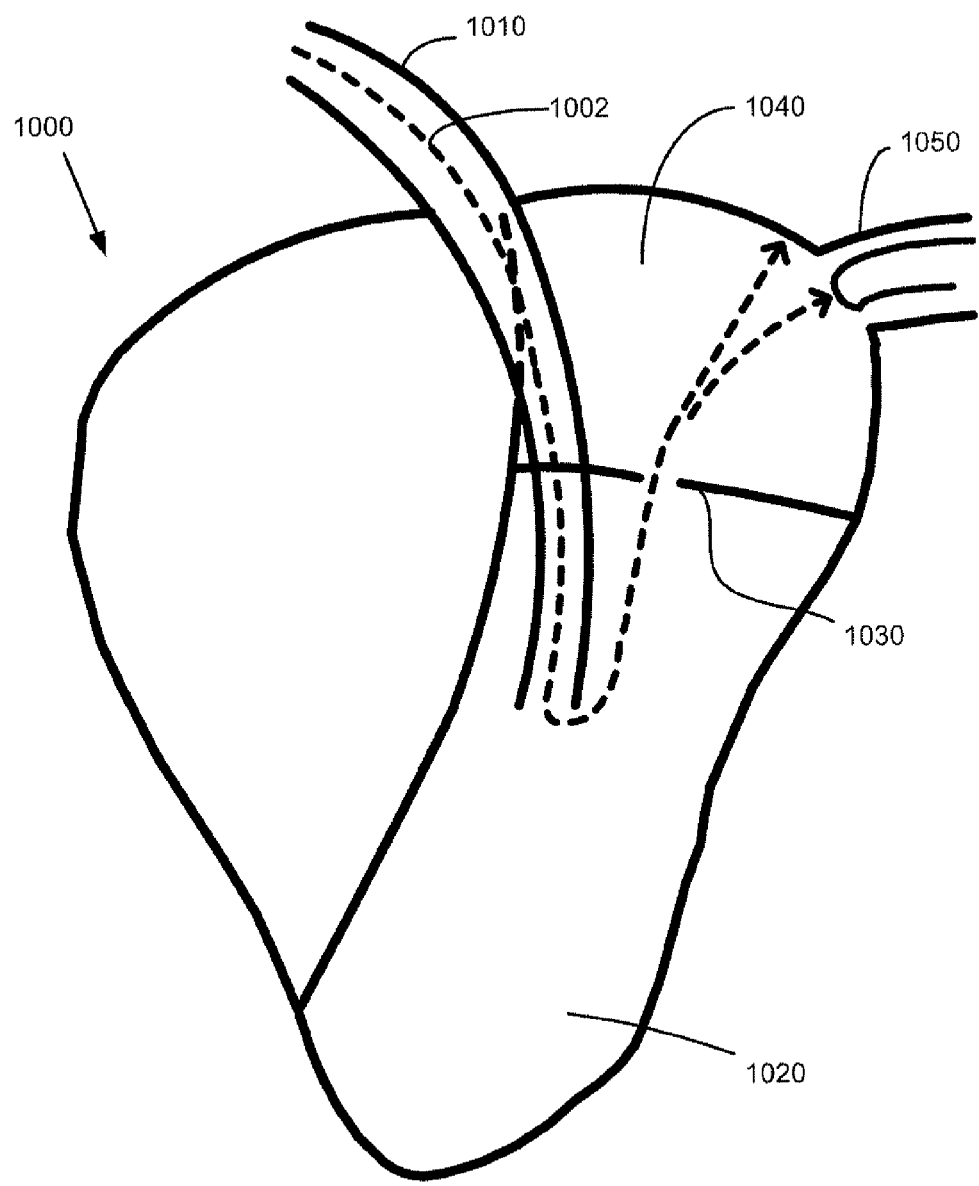
FIG. 10 presents an application of the principles of the present invention to the treatment of left atrium atrial fibrillation.

FIG. 10 schematically presents application of the principles of the invention to the treatment of left atrial fibrillation, 1000. For such a procedure, the catheter 1002 is navigated through aorta 1010 into the left ventricle 1020, and then through the mitral valve 1030 and into the left atrium 1040. From the left atrium, it must be possible to address specific points with the device distal end 1004. Often it is desirable for the ablation pattern to be applied on an arc of a circle around at least one of the pulmonary veins 1050, for fibrillation to be effectively treated. Thus, non-surgical cure for atrial fibrillation is greatly facilitated by improved navigation through convoluted lumen, chambers and valves, selective catheter stiffening, and enhanced distal tip orientation and control in the left atrium, as enabled by the devices and methods of the present invention.

Figure 11:
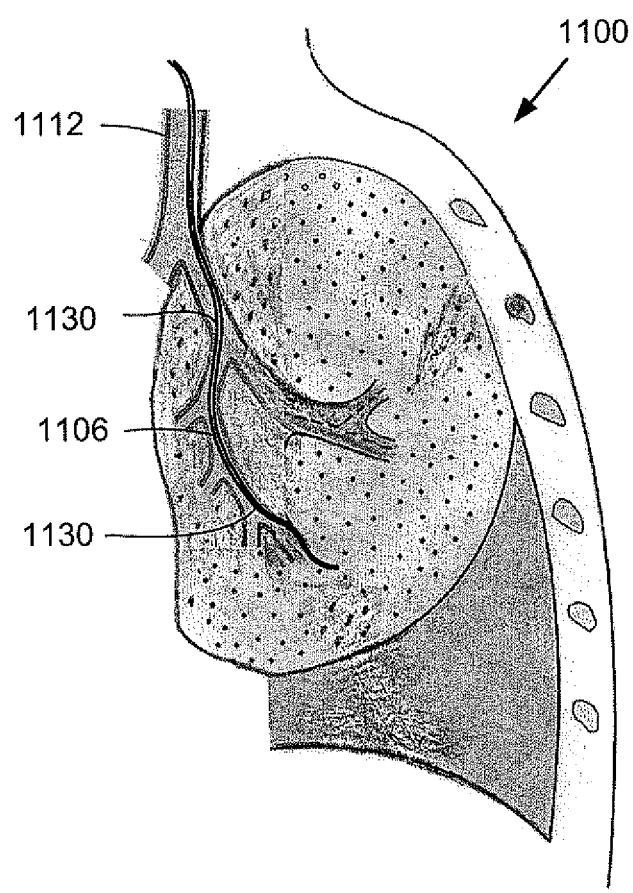
FIG. 11 illustrates application of the principles of the present invention to lung navigation.

FIG. 11 schematically illustrates application of the devices and methods of the present invention to lung bronchial navigation. An interventional device, such as a catheter or bronchioscope 1106, is inserted into the subject's airways and through the trachea 1112, about 20 to 25 mm in diameter. To reach a remote lung nodule or alveoli, the device is navigated through a series of passageways of reducing diameter. In succession after the trachea are the root bronchi (either left or right), followed by the segment bronchi (about 7 mm diameter), that subdivide in the course of seven to eight steps into bronchioles within a specific lobe (with a decreasing diameter from 5 mm to 1 mm). The bronchioles then lead to the membranous lobules and after two or three subdivisions lead to the terminal bronchi. Navigation requires multiple branch decisions, and as such is enabled or greatly facilitated by magnetic steering as known in the art. However, the interventional device has to progress through lumens or widely varying diameter; accordingly it is difficult to proximally transmit forces and torques when advancing the device. There is a tendency for the device to bend, loop, or even prolapse into one of the main lung branches that are not part of the navigation path. The device and method of the present invention provide for selective segment bending or stiffening 1130 of the device through electrostrictive actuators (not shown). Such actuators may be provided substantially along the length of the inserted device, or at least over a length extending proximally to a given distance of the distal tip.

Alternatively or additionally, in one embodiment of the present invention, one or a plurality of piezoelectric elements are imbedded along the length of a medical device. Such elements respond algebraically to tension and compression, and accordingly distinguish between the two states based on an induced voltage polarity. Imbedding piezoelectric elements enable shape feedback and provides and indication of both the amount of local device tensioning and/or bending as well as bending direction. In closed-loop device navigation, the local shape feedback information is taken into account in applying device deflection or actuation means, such as mechanical pull-wires tension, applied electrostrictive tension, applied magnetic fields or magnetic field gradients, and other such device deflection means as known in the art. In particular, the placement of piezoelectric elements in the direct vicinity of medical device deflection or actuation elements permits accurate feedback and more precise navigation control.

In one preferred embodiment, local tension or compression feedback information is leveraged by a virtual device model that predicts the actual device shape under the measured applied tension and compression forces. The use of such a virtual model in conjunction with piezoelectric and electrostrictive devices, enable improved more accurate navigation while limiting the number of such measurement and control devices. When used in combination with additional device navigation means, such as mechanical pull wires and/or magnetic deflection, virtual models provide visual feedback to the user and eliminate much of the "guess work" associated with navigating without such means. Virtual models enable user anticipation of the result of their navigation control commands as well as faster decision with respect to a course of actions to take to achieve a particular navigation diagnostic or therapeutic goal.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A medical device and navigation system combination comprising:
    an elongate medical device having
        a plurality of electrostrictive elements for selectively stiffening portions of the device and a plurality of contact sensors for sensing contact with the medical device; and
        at least one magnetically responsive element associated with a distal end of the elongate medical device for orienting the elongate medical device by applying a magnetic field to cause the distal end of the device to align in a selected direction; and
    a control for actuating one or more of the electrostrictive elements in response to a signal from a contact sensor, to selectively stiffen a portion of the elongate medical device in the vicinity of the sensed contact thereby changing the orientation or response of the elongate medical device achieved by the applied magnetic field compared to when the portion of the elongate medical device is not selectively stiffened.

2. The medical device according to claim 1 wherein the contact sensors are stress sensors that detect and measure a force acting on the medical device.

3. The medical device according to claim 1 wherein the contact sensors are strain gauges that detect and measure deflection of the medical device.

4. The medical device of claim 1 in which the signals associated with the sensing and actuating elements are transmitted to the proximal end of the device by fine wires embedded in non-conducting materials.

5. A magnetically navigable elongate medical device, the device having
    a proximal end,
    a distal end,
    at least one magnetically responsive element associated with the distal end, the at least one magnetically responsive element having sufficient size and shape to orient the distal end of the magnetically navigable elongate medical device in a selected direction in response to an applied magnetic field, and
    a plurality of electrostrictive elements disposed between the proximal and distal ends, which when actuated, change the flexibility or shape of the medical device thereby changing the orientation or response of the medical device achieved by the applied magnetic field compared to when the plurality of electrostrictive elements are not actuated.

6. The magnetically navigable medical device according to claim 5, wherein the magnetically responsive element is of sufficient size and shape to align the medical device in response to an applied field of 0.1 Tesla or less.

7. The magnetically navigable medical device according to claim 6, wherein the magnetically responsive element is of sufficient size and shape to align the medical device in response to an applied field of 0.08 Tesla or less.

* * * * *